(12) United States Patent
Svedman (10) Patent No.: US 6,264,979 B1
(45) Date of Patent: Jul. 24, 2001

(54) TRANSDERMAL DEVICE FOR ADMINISTRATION THROUGH DE-EPITHELIALIZED SKIN

(76) Inventor: Pal Svedman, Ostanvag 85B, 216 19 Malmo, Malmo (SE)

( * ) Notice: Subject to any disclaimer, the term of this patent is extended or adjusted under 35 U.S.C. 154(b) by 0 days.

(21) Appl. No.: 08/737,713

(22) PCT Filed: May 8, 1995

(86) PCT No.: PCT/EP95/01726

§ 371 Date: Nov. 8, 1996

§ 102(e) Date: Nov. 8, 1996

(87) PCT Pub. No.: WO95/30410

PCT Pub. Date: Nov. 16, 1995

(30) Foreign Application Priority Data

May 10, 1994 (GB) .................................................. 9409281

(51) Int. Cl.[7] .......................... A61F 13/02; A61L 15/16; A61K 9/70; A61K 9/127
(52) U.S. Cl. .................... 424/449; 424/448; 424/447; 424/450
(58) Field of Search .................................. 424/449, 448, 424/447, 450

(56) References Cited

U.S. PATENT DOCUMENTS

| | | | |
|---|---|---|---|
| 4,460,370 | 7/1984 | Allison et al. | 604/897 |
| 5,071,656 | * 12/1991 | Lee | 424/448 |
| 5,242,902 | * 9/1993 | Murphy et al. | |
| 5,322,839 | 6/1994 | Voegeli et al. | 514/21 |

FOREIGN PATENT DOCUMENTS

| | | | |
|---|---|---|---|
| 2097163 | 12/1993 | (CA) . | |
| 0 532 465 | 9/1992 | (EP) . | |
| 0 535 530 | 9/1992 | (EP) . | |
| 2 184 016 | 6/1987 | (GB) . | |
| 86-89584 | * 4/1986 | (JP) | A61L/15/01 |
| 90-187075 | * 7/1990 | (JP) | A61K/37/30 |
| 90-204997 | * 8/1990 | (JP) | A61F/13/02 |
| 90-340794 | * 11/1990 | (JP) | A61K/9/70 |
| 91/03271 | 8/1990 | (WO) . | |
| 92/11879 | 1/1992 | (WO) . | |

OTHER PUBLICATIONS

Morimoto, K., et al., "Effects of Proteolytic Enzyme–Inhibitors as an Absorption Enhancer on the Nasal and Transdermal Delivery Systems of Polypeptides," *J. Pharmacobio–Dyn.*, 14:34 (1991).

Verhoef, J.C., et al., "Transport of Peptide and Protein Drugs Across Biological Membranes," *European Journal of Drug Metabolism and Pharmacokinetics*, 15(2):83–93 (1990).

Jacobsson, S., et al., "A New Principle for the Cleansing of Infected Wounds," *Scand. J. Plast Reconstr. Surg.*, 10:65–72 (1976).

* cited by examiner

*Primary Examiner*—Thurman K. Page
*Assistant Examiner*—Brian K. Seidleck
(74) *Attorney, Agent, or Firm*—Flehr Hohbach Test Albritton & Herbert LLP

(57) ABSTRACT

A transdermal device is described suitable for delivery of a pharmaceutical to the systemic circulation through de-epithelialized skin. In its various embodiments the device includes means to prevent the attack of any protein or polypeptide active agent included therein by proteolytic enzymes which exude from the lesion, means to prevent the ingress of bacteria and other cellular debris from the lesion and means to ensure that substantially all said active agent is directed to the de-epithelialized lesion.

19 Claims, 5 Drawing Sheets

TRANSDERMAL DEVICE FOR ADMINISTRATION THROUGH DE-EPITHELIALIZED SKIN

RELATIONSHIP TO OTHER APPLICATIONS

Applicant makes cross-reference to his presently pending U.S. patent application Ser. No. 08/350,488 (filed Dec. 6, 1994) entitled TRANSDERMAL PERFUSION OF FLUIDS, and to his re-examined U.S. Pat. No. B1 5,441,490 (re-examination certificate issued Sep. 16, 1997), entitled TRANSDERMAL PERFUSION OF FLUIDS, and to the application for said patent, U.S. patent application Ser. No. 84,267 (filed Jan. 7, 1992, PCT).

FIELD OF THE INVENTION

BACKGROUND OF THE INVENTION

The invention relates to a device for delivery of a pharmaceutical to the systemic circulation of a human or animal body via the skin, and in particular, via skin from which the epidermis has been removed.

The administration of pharmaceuticals through the skin is a concept which is now well-established. Transdermal administration has several advantages over more conventional forms of drug delivery such as injection or oral ingestion. Transdermal devices can provide sustained and controlled release of the active agent over a prolonged period so that the resulting blood levels remain constant. This is in contrast to administration, by injection, for example where surges of the agent occur in the bloodstream immediately after administration and then drop away rapidly until the next dose is given. In the case of oral administration the blood level is further influenced by the contents of the intestines and is therefore difficult to control. Transdermal administration permits direct access to the bloodstream without first passage through the gastro-intestinal tract and liver. In addition, transdermal administration is more convenient and comfortable for patients because a small device or plaster can remain attached to the skin for a prolonged period without patient intervention. The inconvenience of administering drugs at regular intervals orally or by injection is therefore avoided.

Despite the aforementioned advantages, the number and type of pharmaceutically active agents which have been successfully given transdermally is limited. This is because the epidermis provides a natural barrier against the ingress of foreign substances into the body and there are few drugs which are able to adequately permeate this barrier of their own accord. One approach to this problem has been to include in transdermal devices so-called permeation enhancers, molecules which are able to increase the uptake of an active agent through the skin. A particular example is diethyltoluamide although many others are known to the skilled man in this field. The use of permeation enhancers has increased the number of drugs which may be given transdermally and because of the lipophilic nature of the epidermis there has been reasonable success with drugs which are relatively hydrophobic molecules. The steroid hormones are a particular example. In addition to the use of permeation enhancers, electrochemical means have also been used to promote drug transport across the epidermis with some success.

However, notwithstanding these methods the epidermis is a very effective barrier against hydrophilic substances which has hitherto rendered transdermal administration of drugs falling in this category very difficult, if not impossible. Thus the increasing number of potent pharmaceuticals which are proteins and polypeptides cannot generally be administered transdermally.

SUMMARY OF THE INVENTION

To overcome the aforementioned problems the present inventor has developed a technique for circumventing the epidermal barrier by administering a drug transdermally through a patch of skin which is de-epithelialized i.e. has a portion of the epidermis absent, whether or not deliberately removed.

A standardized de-epithelialized lesion of pre-determined size can be made using a device such as that described in the Applicants' co-pending International Application WO92/11879. This device when attached to the skin applies suction to delaminate the epidermis from the dermis and so form a blister containing a clear blister fluid. The roof of the blister comprises the epidermis and can easily be removed leaving a standard-sized de-epithelialized lesion where the dermis is exposed. Typical lesions are about 4 to 6 mm in diameter and about 200 $\mu$m to about 1000 $\mu$m deep when made on the lower forearm for example. Where the epidermis is thicker e.g. sole of the foot a lesion of 2 mm to 4 mm would be expected. The lesions are suitable for the application of a drug-loaded transdermal device.

The passage of pharmaceutically active agents through the skin to the bloodstream has been demonstrated to be much improved where the skin is de-epithelialized. Further, it has been shown by the present inventor that de-epithelialized skin allows transdermal administration of hydrophilic drugs such as proteins, polypeptides and polysaccharides. In a paper by the inventor in the Lancet Vol 337 June 1991, successful transdermal delivery of the vasopressin analogue 1-deamino-8-D-arginine vasopressin through a de-epithelialized skin lesion is described. The inventor has also achieved successful administration of the polypeptide human growth hormone and the polysaccharide anti-thrombotic agent, Fragmin. Once treatment is complete and the device removed, the de-epithelialized lesion heals without scarring and accordingly it is not substantially more inconvenient than applying a transdermal device directly to the epidermis.

While there are clearly advantages to transdermal administration of pharmaceutically active agents through de-epithelialized skin, i.e. a lesion of about 200 $\mu$m to about 1000 $\mu$m in depth with the dermis exposed, certain problems are encountered when applying a transdermal device to an open wound which do not arise when applying a device to intact skin. Firstly the device will be susceptible to the ingress of exudate from the wound. The suction injury elicits acute inflammation within 24 hours which brings polymorphs and macrophages to the wound site. The exudate will include bacteria, whole cells, cellular debris and enzymes, in particular proteolytic enzymes which will interfere with the proper functioning of the device. Proteolytic enzymes will of course be particularly damaging when the drug being delivered is a protein or polypeptide. The present invention is thus concerned with improved transdermal devices which are suitable for use on de-epithelialized skin which include features to overcome the aforementioned problem and with methods of using them for transdermal administration.

Secondly, in a method of administering an active agent transdermally through a de-epithelialized skin lesion it is desirable to ensure that substantially all of the active agent is taken up by the lesion and not lost to portions of intact epidermis and/or in adhesive layers of the device. The present invention is thus also concerned with transdermal devices which ensure efficient delivery of the active agent within the area of the lesion and with methods of using such devices for transdermal administration.

In accordance with a first aspect of the invention there is provided a transdermal device suitable for administration of an active agent to the systemic circulation through a de-epithelialized skin lesion which device is provided with means to prevent the attack of any protein or polypeptide active agent included therein by proteolytic enzymes which exude from said de-epithelialized lesion.

In accordance with a second aspect of the invention there is provided a transdermal device suitable for administration of at least one pharmaceutically active agent to the systemic circulation through a de-epithelialized skin lesion wherein said device is provided with means to de-activate bacteria entering the device from the lesion and/or to prevent the ingress of said bacteria and other cellular debris.

In accordance with a third aspect of the invention there is provided a transdermal device suitable for administration of at least one pharmaceutically active agent to the systemic circulation through a de-epithelialized skin lesion wherein said device is provided with means to ensure that substantially all said active agent is directed to the de-epithelialized area within the boundaries of said lesion.

In accordance with a fourth aspect of the invention there is provided a method of administering a pharmaceutically active agent to the systemic circulation of a human or animal body comprising:

(a) for an area of skin of pre-determined size, delaminating the epidermis from the dermis, (b) removing said delaminated epidermis to form a de-epithelialized skin lesion, also of pre-determined size and (c) applying to said lesion a transdermal device in accordance with the first, second or third aspects of the invention.

In accordance with a fifth aspect of the invention there is provided a method of administering a pharmaceutically active agent to the systemic circulation of a human or animal body comprising:

(a) for an area of skin of pre-determined size, delaminating the epidermis from the dermis, (b) removing said delaminated epidermis to form a de-epithelialized skin lesion also of pre-determined size and (c) applying to said lesion a flexible plaster or patch of laminar structure which is loaded with or adapted to be loaded with the pharmaceutically active agent, or applying a topical preparation which comprises said agent, the agent preferably having a molecular weight of greater than 1000 Daltons.

In accordance with the first and second aspects of the invention a transdermal device which includes means for preventing attack of the active agent by proteolytic enzymes and/or includes means to de-activate or prevent the ingress of bacteria and cellular debris from the wound may be of any known construction. It may be a rigid device comprising a housing made from, for example plastic or fibreglass in which is contained at least one reservoir carrying the pharmaceutically active agent. For example it may be a device such as that described in the inventors' copending International Application WO92/11879. Alternatively it may be a patch or plaster having a laminar construction which is well-known in the art of transdermal delivery. In the case of either type of device the reservoir for carrying the pharmaceutically active agent may be a chamber for containing the agent either as a solid or in an unsaturated, saturated or supersaturated solution or in a suspension, the bottom wall of the chamber located nearest the skin being of a material permeable to the active agent.

A more common form of drug reservoir however, in a transdermal device, is an inert porous matrix in which the active agent may be dispersed, in particulate form or as an unsaturated, saturated or supersaturated solution. Many materials have been used to prepare such a matrix. For example, hydrogels which comprise a very large class of materials with characteristic swelling and diffusional properties, can be used. Biocompatible hydrogels for drug delivery applications may be based on polymers like hydroxyethylmethacrylate, poly(ethylene glycols) and poly (ethylene oxide). These materials can be cross-linked by radiation or by other known methods to provide water-insolubility. In manufacture a water-soluble drug is mixed with a dry hydrogel which absorbs the water into its matrix and so swells.

Charged polymers of the type used in ion-exchange and electrodialysis may also provide a suitable porous matrix for the active agent. Positive ionic groups e.g. tertiary ammonium groups or negative ionic groups e.g. sulphonic acid groups, are coupled to the polymer backbone.

Hydrocolloids manufactured by direct compression of powder such as methylhydroxypropyl cellulose or polyvinyl alcohol can be useful as an inert porous matrix for the active agent as well as numerous other synthetic and natural polymers known to the skilled man.

Many of these will in themselves be adhesives which avoids the need to add an additional adhesive layer to the laminate structure for attachment to the skin. Particularly preferred for transdermal use are acrylate, silicone and polyisobutylene adhesives which are capable of forming a porous matrix suitable as a reservoir for the active ingredient. Hydrocolloid adhesives are particularly useful because they can absorb water from the intact skin layer without reducing the integrity of the adhesive. This is important when the device needs to be maintained on the skin for several days. Even acrylate and silicone adhesives when not used as a drug matrix can be made sufficiently porous to channel excess water forming on the skin.

For active agents which are macromolecules such as polypeptides and polysaccharides a matrix of relatively large pore size will be required. Whatever the nature of the transdermal device, where it is loaded with or designed for loading with an active ingredient which is a protein or polypeptide the active agent will require protection from proteolytic enzymes which exude from the wound. One way in which this may be done is to provide a physical barrier between the skin surface and the drug reservoir. Such an arrangement is possible where the protein or polypeptide active agent is of a molecular size which is smaller than that of the average proteolytic enzyme. This is in fact the most usual situation since a number of protein drugs currently available are small polypeptides whereas proteolytic enzymes usually have a molecular weight in excess of 100,000 Daltons.

Thus the physical barrier may comprise a selective membrane positioned so as to be between the drug reservoir and the de-epithelialized skin when the device is in use, the membrane having such pore size as to block the passage of proteolytic enzymes exuding from the de-epithelialized skin while permitting passage of the protein or polypeptide active agent to the skin.

Alternatively the inert porous matrix itself may provide the physical barrier by being of such pore size as to block the passage of proteolytic enzymes into the device. Ideally the membrane or the inert porous matrix should have a pore size which allows the passage of the active agent from the reservoir to the skin while preventing the passage of proteins having a molecular weight greater than 100,000 Daltons and where appropriate, preventing the passage of proteins with a molecular weight greater than 50,000. Preferably the membrane or inert porous matrix has an average pore size of about 50 Å diameter.

Suitable materials for a selective membrane include cellulose acetate, nitrocellulose, polytetrafluoroethylene, swollen hydrogels as discussed above and many other synthetic and natural polymers. The membrane or inert matrix may vary in pore size across the depth so that the pores become wider in the direction of movement of the active agent.

A transdermal device in accordance with the first aspect of the invention may include both a drug reservoir which is an inert polymer matrix of pore size which will exclude proteolytic enzymes and an appropriate selective membrane as described above.

The transdermal device may further include a pre-filter which in use is positioned between the selective membrane or inert polymer matrix and the de-epithelialized skin. The pre-filter is a membrane of larger pore size, preferably more than 10 times the pore size of the selective membrane or inert porous matrix and more preferably pore size about 0.2 to 15 μm, which may be made from for example a cellulose ester, polypropylene or polyvinylidene difluoride although other polymeric materials may be used. The pre-filter serves to block larger particles such as cellular debris and bacteria from entering the device so that the selective barrier to proteolytic enzymes does not become clogged with these particles and so prevent the passage of the active agent to the de-epithelialized skin.

Clogging of the device may be further prevented by impregnating any selective membrane, pre-filter or porous matrix with an anti-coagulant to hinder formation of blood clots.

In another embodiment of the invention a protein or polypeptide active agent is protected from attack by proteolytic enzymes by inclusion in the device of at least one proteolytic enzyme inhibitor. The suction injury will elicit a response comprising hemostasis, inflammation, fibroblast proliferation, angiogenesis, connective tissue synthesis and epithelialization. The element of haemorrhage will expose blood to collagen, which activates the Hagemann factor and causes degranulation of platelets. The combined effects of activated Hagemann factor and tissue injury set into action four biochemical amplification systems, the complement cascade, the intrinsic coagulation mechanism, the kinin cascade and the fibrinolytic system. Acute inflammation is established within 24 hours and polymorphonuclear leucocytes, macrophages and mast cells enter the wound.

Enzymes which are released from these cells include aminopeptidases, carboxylpeptidases, endopeptidases and dipeptidylpeptidase. Bestatin, amastatin, phosphoramydon or cholate and its analogues are suitable as inhibitors for these categories of enzymes. Specific peptidases likely to be present in the wound are collaginase and elastase both of which can be inhibited by $\alpha_2$-macroglobulin. Where metalloproteases are present e.g. $Ca_2+$ dependent elastase, chelators such as sodium ethylenediaminetetraacetic acid will inhibit activity. Other proteolytic enzymes which may be present are, for example, plasmin and plasminogen activator for which specific inhibitors are known.

It is not discounted that the proteolytic enzyme's normal substrate could function as the inhibitor in the device.

It is also possible to include inhibitors of a non-specific nature such as steroid hormones which generally inhibit release of collaginase, neutral proteases and plasminogen activator. Similarly, non-steroidal anti-inflammatory drugs can inhibit the enzyme release process.

Finally, the pH of the reservoir may be adjusted to reduce proteolytic enzyme activity. A pH of >8.5 or <6.5 will result in a general inhibition.

An enzyme inhibitor may be included in the drug reservoir and/or in any selective membrane or pre-filter as described above which acts as a physical barrier and/or it may be prepared in solution with the active agent. It is preferable if the inhibitor is retained in the device in a permanent or semi-permanent manner so that it does not migrate into the skin with the active agent or migrates at a very much slower rate (zero order kinetics) than the active agent. This may be achieved in a number of ways.

Protease inhibitors, particulalry peptides, can be chemically immobilized to membranous materials or other solids within the device by routine procedures known for enzyme immobilization. As a particular example, peptides can be bound to starches and other polysaccharides formed into porous films e.g. sephadex film.

An alternative is to provide within the device a saturating level of a substrate of the proteolytic enzyme to be inhibited. If such an enzyme enters the device from the wound it will be immediately engaged with the excess of substrate and will not be available to attach the polypeptide active agent.

Yet another way of keeping the proteolytic enzyme inhibitor in the device is to incorporate within a drug loaded matrix, one or more discrete reservoirs containing the inhibitor. The reservoir may comprise an outer non-porous wall over an inner wall incorporating a semi-permeable membrane. The outer wall is of a material which will fracture, or otherwise become porous, if a small amount of compression is applied to the device. This allows very slow release of the inhibitor into the drug matrix which is concentration driven and which exhibits zero order kinetics.

In another embodiment of the invention the active agent is protected from attack by proteolytic enzymes exuding from the wound by encapsulating molecules of a protein or polypeptide active agent in microspheres or liposomes. The microsphere or liposome preparation then replaces the conventional drug reservoir as described above.

Microspheres are spherical particles with a diameter in the range from about 10 nm to 2 mm which can be made from a variety of natural and synthetic polymers and which may be prepared with an active agent encapsulated therein. Suitable materials for the formation of microspheres are, for example cross-linked dextrans and ceramic materials. Also suitable are a large range of synthetic polymers such as polyurethanes, polymethylmethacrylate, polyethylene terephthalate, polystyrene, polyolefin, polyacrylamide, polylactide, polyglycolide, and other synthetic polymers used in biomedical applications. The microsphere provides a protective physical barrier to the ingress of proteolytic enzymes providing it has a pore size which blocks the passage of proteins having a molecular weight greater than 100,000 or where appropriate greater than 50,000.

Liposomes are spherical lipid vesicles in which the walls of the sphere are lipid monolayers or bilayers having a similar structure to a cell membrane. Methods are well-known for preparing liposomes so that they encapsulate other materials. The liposome membrane provides a barrier against the ingress of proteolytic enzymes so that protection for an active agent which is a protein or polypeptide is thereby achieved in accordance with the invention.

In yet another embodiment of the invention an active agent which is a protein or polypeptide can be protected from attack by proteolytic enzymes by being included in the device in a modified form which is resistant to such attack. For example pro-drugs can be prepared by condensing peptides with a free N-terminal amino group with aldehydes and ketones (e.g. 4-imidazolidine pro-drug derivatives).

Such pro-drugs are not only resistant to enzymic attack but are readily hydrolysed to the parent peptide in aqueous solution so that they may be maintained in the device in a non-aqueous phase and become activated when they reach the aqueous environment of the wound.

A device in accordance with the first aspect of the invention which includes means for preventing attack of an active agent by proteolytic enzymes may incorporate as the active agent peptides and proteins such as, for example vasopressin, human growth hormone, insulin, interferon, interleukins, erythropoietin or calcitonin.

In accordance with the second aspect of the invention a transdermal device is provided suitable for use on de-epithelialized skin which includes means to deactivate bacteria entering the device and/or to prevent ingress of said bacteria and cellular debris which exude from the wound. Such a device may also include any of the structural, chemical or biochemical features discussed above.

In one embodiment the means to block the ingress of bacteria and cellular debris is a physical barrier such as a pre-filter as discussed above, preferably having a pore size of about 0.2 to 15 $\mu$m, which can be made from cellulose esters, polypropylene, polyvinylidene difluoride or a swellable hydrogel. Such a material may be used to form the drug reservoir either by forming a matrix in which the active agent is dispersed or forming a chamber containing a liquid with the active agent in the form of a solid or in an unsaturated, saturated or supersaturated solution or in suspension. Microspheres and liposomes also provide a physical barrier to the ingress of bacteria and cellular debris. As aforementioned the barrier material may be impregnated with an anti-coagulant to prevent clogging.

In another embodiment proliferation of bacteria in the drug reservoir of a transdermal device is prevented by including therein an anti-bacterial agent as well as the active agent to be delivered through the skin. The anti-bacterial agent may be an antibiotic, preferably one commonly chosen for treating skin disorders such as neomycin, bactracin or polymyxin B. The anti-bacterial agent can be included in the drug reservoir with the active ingredient or where the reservoir is a chamber, impregnated in the walls thereof. The anti-bacterial agent may also be included in any selective membrane, pre-filter, microsphere or liposome as described above.

As an alternative anti-bacterial agent to an antibiotic, silver or compounds thereof may be used in the transdermal device. In particular silver chloride, silver nitrate, silver oxide, silver hydroxide or silver sulphadiazine will all have a bactericidal effect. As with antibiotics, the silver compounds may be dispersed in a porous matrix with the active agent or impregnated into the walls of the drug reservoir or any barrier membrane or pre-filter as described above. For example, an activated charcoal membrane impregnated with silver or silver chloride is useful for the absorption and elimination of bacteria. Silver and silver compounds may also be incorporated into microspheres during preparation.

In a further embodiment the anti-bacterial agent may be a conserving agent such as metagine or propylene glyol incorporated into the device in the same way as other anti-bacterial agents.

As with peptide inhibitors embodiments of this second aspect of the invention include devices in which the anti-bacterial agent is permanently or semi-permanently incorporated therein so that transdermal uptake of the anti-bacterial agent is substantially avoided. For example, the anti-bacterial agent could be incorporated as one or more discrete reservoirs in the drug matrix as with the peptide inhibitors described above. The anti-bacterial agent may then be slowly released into the matrix by compression of the device.

As an alternative the agent can be chemically or physically bound to a suitable matrix. For example, iodine can be conveniently bound to a polyvinylalcohol. Other materials suitable for impregation with, for example, silver and its compounds are collagen and elastin.

As an alternative to an anti-bacterial agent, bacterial proliferation in the device may be reduced by adjusting the pH of the drug reservoir. Bacteria which are associated with the skin lesion will not be able to grow at a pH of 5.5. or below.

Finally, in yet another embodiment in accordance with the second aspect of the invention, bacteria and other debris which may have entered the device from the wound exudate can be absorbed on to a surface treated to enhance bacterial adherence, in particular a surface treated with a hydrophobic substance. For example, a fatty acid ester such as dialkyl-carbamoylchloride may be bound to surfaces adjacent to the drug reservoir. If the active agent is in an aqueous solution, the common skin pathogens which enter the solution and which have a hydrophobic surface adhere to the treated surface by hydrophobic interaction and are thus kept away from the preparation of the active agent.

In accordance with the third aspect of the invention a transdermal device is provided which includes means to ensure that substantially all of the pharmaceutically active agent is directed to the de-epithelialized area within the boundaries of the skin lesion. This is preferably achieved by having a single aperture approximately the same size as the skin lesion. Such a device may be a solid structure such as that described in the applicants' co-pending Application No WO92/11879 or a patch or plaster of a type well-known in the art.

In a typical embodiment the means to ensure that substantially all the active agent reaches the lesion is a layer of impermeable material suitably positioned between the lower side of the drug reservoir and the de-epithelialized skin, the impermeable material having a single central aperture approximately the same size as the de-epithelialized lesion. Preferably, the single aperture covers 5–20% of the total area of the device in contact with the skin. Typically, the impermeable layer is positioned between the drug reservoir and any adhesive layer included in the device. The effect of the impermeable layer is to prevent the active agent sinking into adhesive from which it may not then be released into the lesion or sinking into the area of intact skin around the lesion from where it is unlikely to reach the bloodstream.

In order to ensure that the central aperture is positioned directly over the de-epithelialized lesion the device may be formed of materials which are substantially transparent.

A device having means to efficiently direct the active agent to the de-epithelialized lesion may also include any of the features described herein in connection with the first and second aspects of the invention.

In its fourth and fifth aspects the invention is concerned with methods of administering pharmaceutically active agents through a de-epithelialized skin lesion, particularly those which are larger molecules having a molecular weight in excess of 1000 Daltons and/or which are hydrophilic and could not be given by conventional transdermal administration to intact skin. The inventors have shown using fluorescein-labelled dextrans that molecules of from 3000 to 70,000 molecular weight can be efficiently administered transdermally through de-epithelialized skin. Such a molecular weight range includes many bio-active proteins and polypeptides. Of course any transdermal device, including the features described above, may be applied in the method of the invention. Furthermore the application of topical preparations to the de-epithelialized lesion is not excluded.

Other features and advantages of the invention will appear from the following description in which the preferred embodiments have been set forth in detail, in conjunction with the accompanying drawings.

The invention will now be described by way of example with reference to the accompanying drawings and examples.

DETAILED DESCRIPTION OF THE PREFERRED EMBODIMENTS

Figure 1:
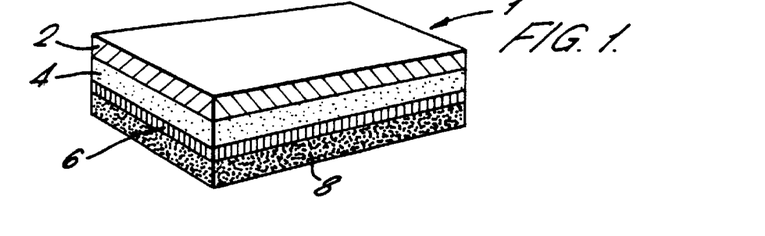
FIG. 1 shows a transdermal device of the patch type in accordance with the first aspect of the invention, including a selective membrane.

Referring first to FIG. 1 the device 1 is of the well-known laminar structure comprising an impermeable backing material 2 which may be, for example, an impermeable aluminized polyester film, which is laminated by heat sealing to a drug reservoir layer 4. The drug reservoir is of the matrix type in which the active agent is dispersed in a porous material in an unsaturated, saturated or supersaturated solution or in a suspension or in solid form. The drug reservoir 4 is laminated to a selective membrane 6 made from, for example, cellulose acetate having a pore size which will exclude enzymes of molecular weight greater than 50,000 or where appropriate 100,000. The drug reservoir 4 is thus protected from the ingress of proteolytic enzymes, bacteria and other cellular debris. A contact adhesive 8 generally of the acrylate or silicone type, is laminated to the selective membrane 6.

Figure 2:
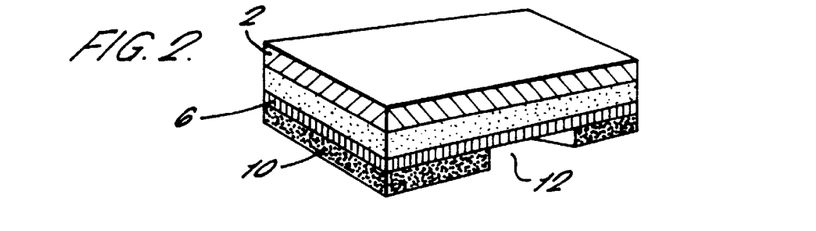
FIG. 2 shows a transdermal device similar to FIG. 1 with a portion of the contact adhesive removed.

The device of FIG. 2 includes all the components of FIG. 1 except that adhesive 10 is absent at the point 12 where the device will be in contact with the de-epithelialized skin lesion. Transfer of the active agent to the skin is thus not hindered by the adhesive but the ingress of proteolytic enzymes, bacteria and other cellular debris to the drug reservoir is prevented by the selective membrane 6.

Figure 3:
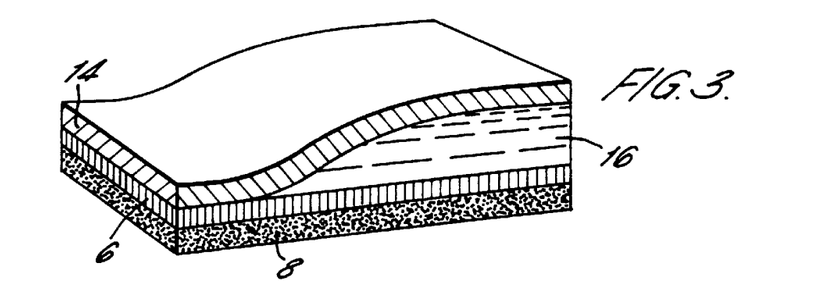
FIG. 3 shows a transdermal device of the patch type according to an alternative embodiment of the first aspect of the invention.

FIG. 3 shows an alternative type of transdermal device in the form of a patch or plaster which comprises an impermeable backing material 14 such as that mentioned above, laminated to a drug reservoir 16 of the liquid-filled chamber type. The bottom of the drug reservoir is formed by a selective membrane 6, similar to that shown in FIGS. 1 and 2, which in turn is laminated to an adhesive layer 8.

Figure 4:
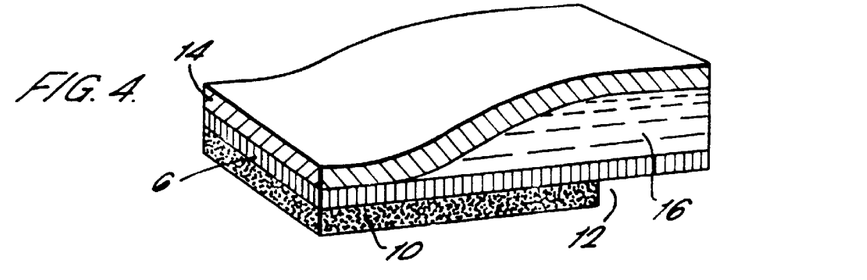
FIG. 4 shows a transdermal device similar to FIG. 3 with a portion of the contact adhesive removed.

FIG. 4 is a device similar to that of FIG. 3 but with the adhesive 10 absent at the point 12 where the device will be in contact with the de-epithelialized skin which has advantages as mentioned above.

Figure 5:
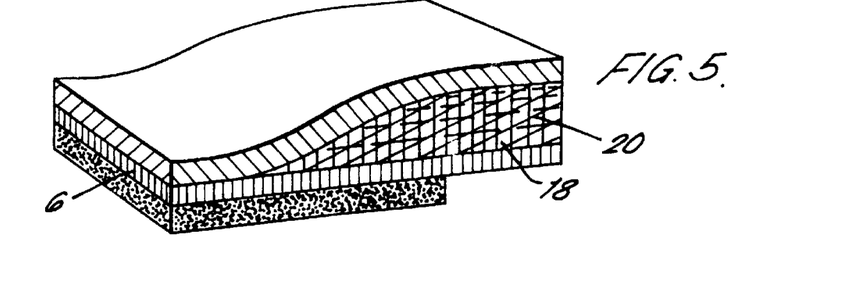
FIG. 5 shows a transdermal device in accordance with another embodiment of the first aspect of the invention.

FIG. 5 shows an alternative embodiment to that shown in FIG. 4 in which the liquid-filled reservoir 18 incorporates a hydrophobic, compression resistant, woven material forming a capillary active matrix 20. Bacteria which have successfully transgressed the selective membrane 6 may be removed from the drug solution by adhering to the hydrophobic weave.

Figure 6:
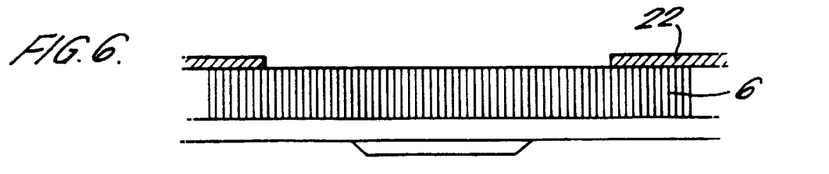
FIG. 6 is a diagrammatic representation of part of a transdermal device in accordance with the first and third aspects of the invention having a selective membrane and barrier layer.
Figure 7:
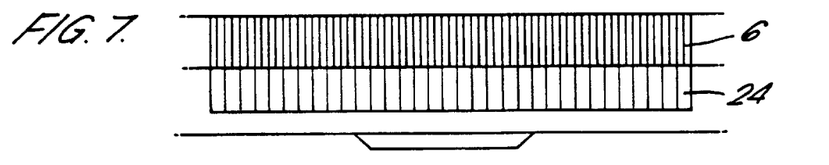
FIG. 7 is a part of a transdermal device in accordance with the first aspect of the invention including a selective membrane and pre-filter.

FIG. 6 shows in more detail the portion of the transdermal device which comprises the selective membrane 6. In the embodiment of FIG. 6 an impermeable barrier layer 22 is provided around the periphery of the upper surface of the membrane 6 separating the peripheral portion of said membrane from the drug reservoir. This ensures that drug delivery is concentrated only on the de-epithelialized lesion 23 and is not lost in the selective membrane 6 or adhesive layer.

Figure 8:
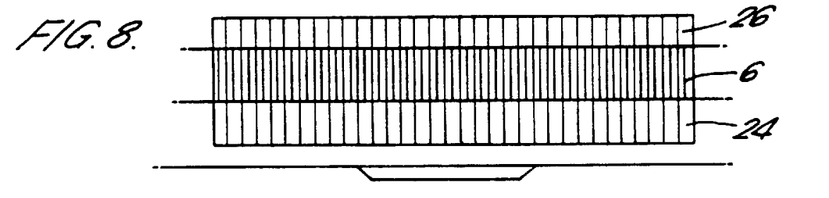
FIG. 8 is a part of a transdermal device in accordance with the first aspect of the invention including an additional pre-filter.
Figure 9:
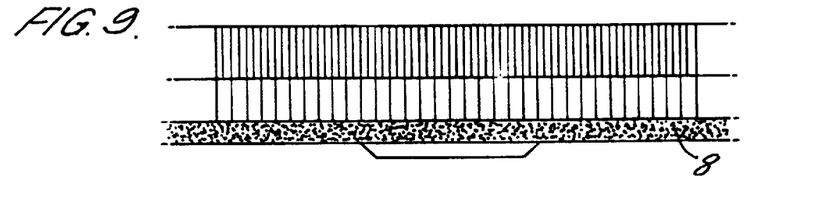
FIG. 9 is part of a transdermal device as shown in FIG. 7 but including an adhesive layer.
Figure 10:
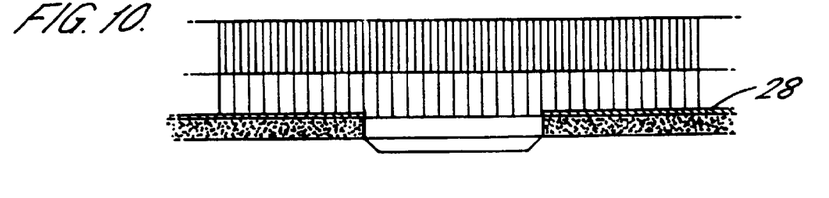
FIG. 10 is part of a transdermal device similar to that shown in FIG. 9 but including a portion of the adhesive removed and an additional impermeable barrier.

FIGS. 7 to 10 all show embodiments which include a pre-filter 24 of larger pore size than the selective membrane 6. In FIG. 8 two pre-filter layers are provided one 24 below and one 26 above the selective membrane 6. The device of FIG. 9 is the same as that of FIG. 7 except that the contact adhesive layer 8 is shown. FIG. 10 shows a further embodiment in which a barrier 28 of an impermeable material, such as aluminized polyester film, is included around the periphery of the device between the lower surface of the pre-filter 24 and the adhesive layer 8. Such an arrangement ensures that all of the active ingredient is channelled to the de-epithelialized spot 23 and not lost in the adhesive 8.

Figure 11:
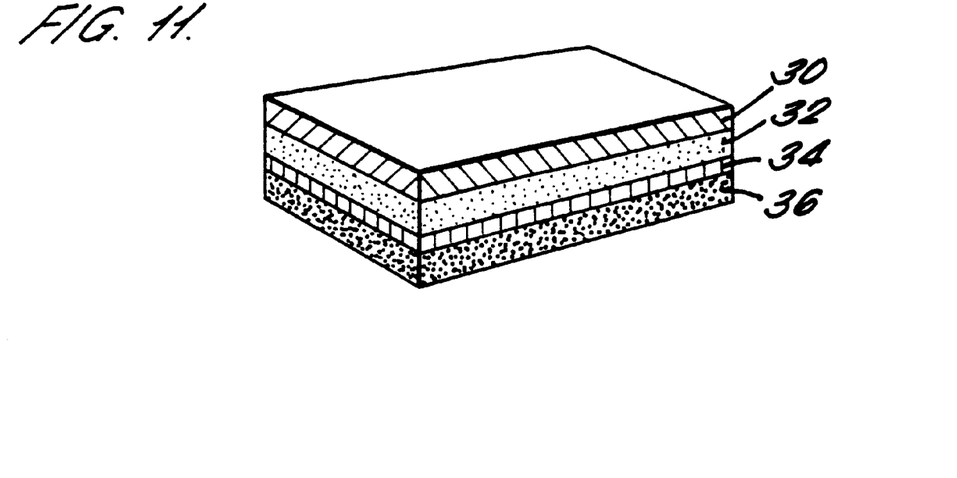
FIG. 11 shows a transdermal device in accordance with the second aspect of the invention.

The device shown in FIG. 11 is one in accordance with the second aspect of the invention and comprises an impermeable backing layer 30 which may be for example, an impermeable aluminized polyester film, laminated to a drug reservoir layer 32. The drug reservoir 32 is of the matrix type in which the active agent is dispersed in a porous material in an unsaturated, saturated or supersaturated solution or in suspension or other solid form. The drug reservoir 32 is laminated to a filter 34 which is a porous material of, for example, cellulose ester, polypropylene or polyvinylidene difluoride having a pore size in the region of about 0.2 to 15 $\mu$m. The filter serves to block the ingress of bacteria and other cellular debris from the wound exudate into the drug reservoir. The filter 34 is laminated to an adhesive layer 36.

Figure 12:
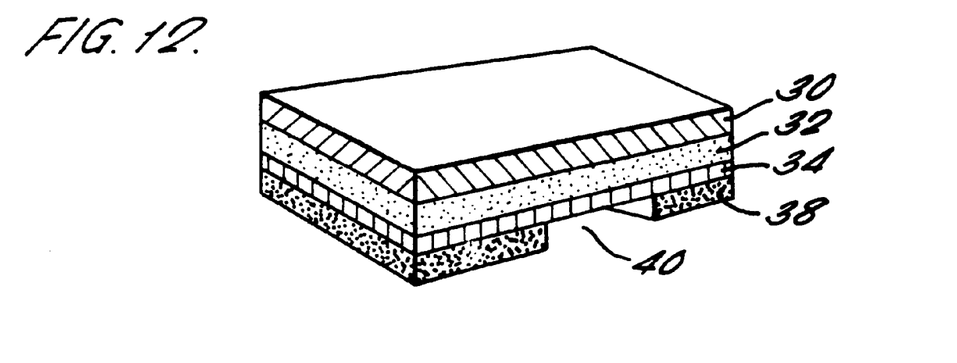
FIG. 12 shows a transdermal device in accordance with the second aspect of the invention with a portion of the adhesive removed.

FIG. 12 shows an alternative embodiment to that of FIG. 11 in which part of the adhesive layer 38 directly overlying the de-epithelialized spot is absent so allowing a free passage of the active agent to the skin.

Figure 13:
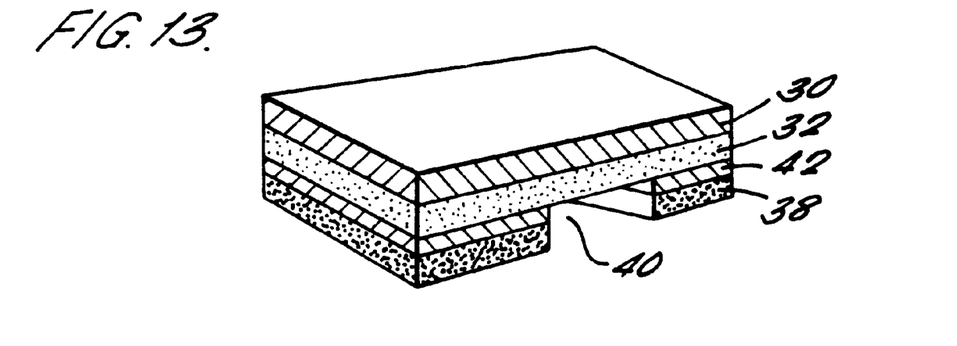
FIG. 13 shows a transdermal device in accordance with the third aspect of the invention with an impermeable barrier layer.

A device in accordance with the third aspect of the invention is shown in FIG. 13 and comprises an impermeable backing layer 30 laminated to a drug reservoir 32 of the matrix type as described above. Laminated to the reservoir 32 is an annular layer 42 of an impermeable material such as aluminized polyester film, having a central aperture 40 approximately the size of the de-epithelialized spot. The impermeable layer is laminated to an annular layer of adhesive 38. The layer 42 prevents active agent from the matrix 32 passing into the adhesive 38 where either it may not be released to the skin or, if it comes into contact with intact skin cannot be absorbed into the bloodstream.

Figure 14:
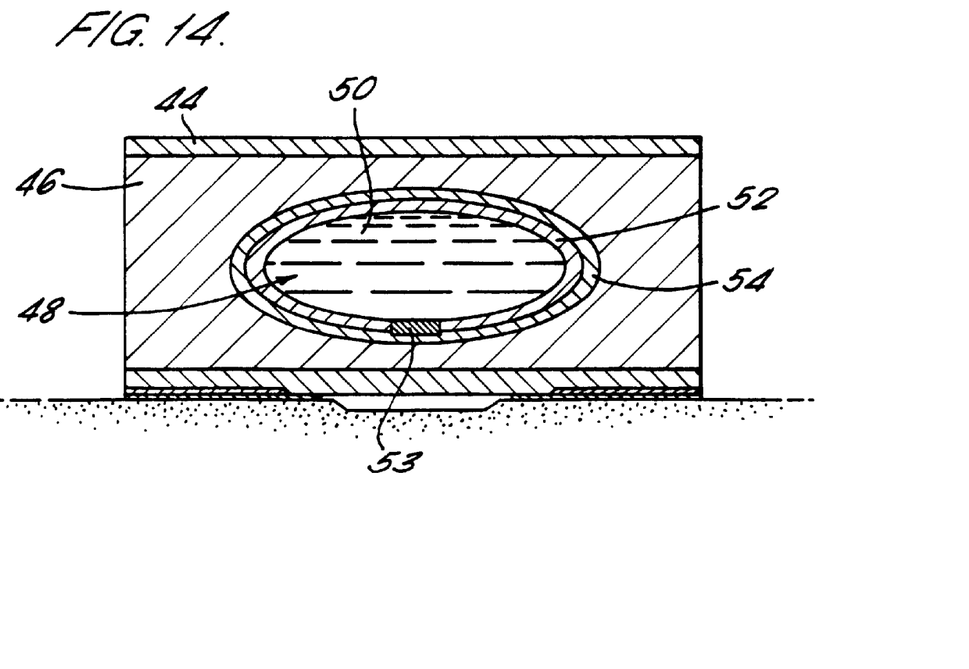
FIG. 14 shows a device in accordance with any aspect of the invention where enzyme inhibitor or anti-bacterial agent is held in a discrete reservoir within the drug matrix.
Figure 15:
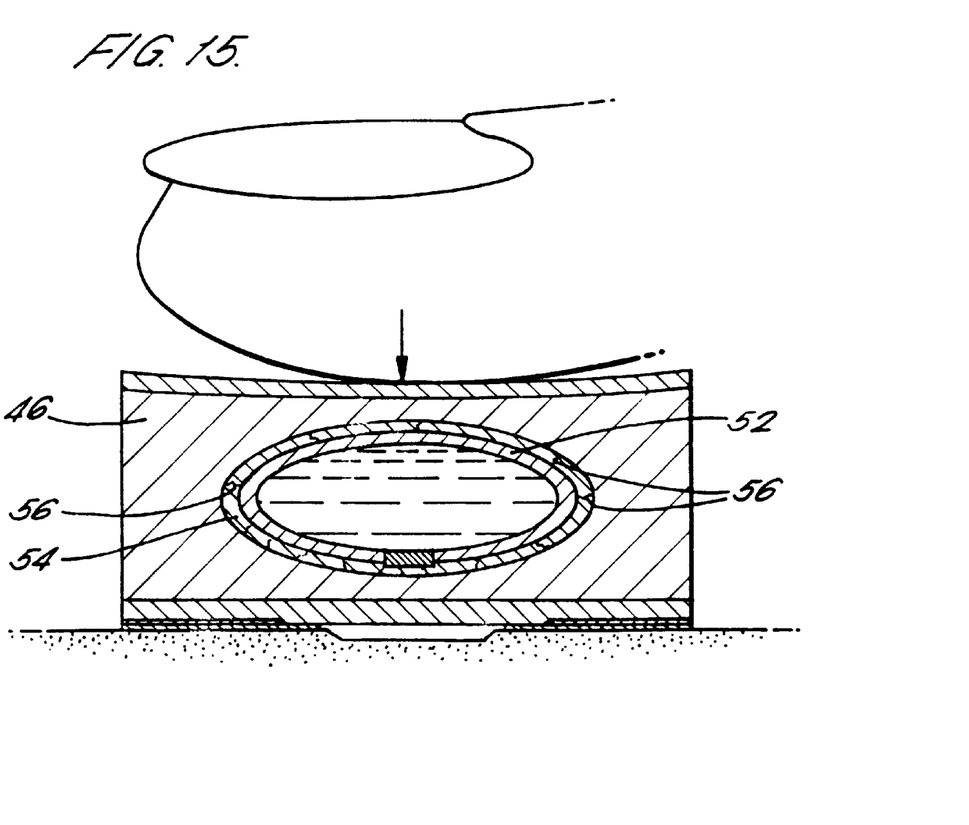
FIG. 15 shows the device of FIG. 14 under compression and FIG. 16 shows a device according to any aspect of the invention having means to control ingress of water from the intact skin.

FIGS. 14 and 15 show a device which may be one in accordance with any of the three aspects of the invention which provides means for very slow release of any peptide inhibitor or anti-bacterial agent into the drug matrix of the device. In this particular embodiment the device has an impermeable backing layer 44 laminated to a drug reservoir 46 of the matrix type as hereinbefore described. Within the matrix 46 a reservoir 48 is included which contains the enzyme inhibitor or anti-bacterial agent 50. The reservoir has outer and inner walls. The inner wall 52 is a slightly elastic impermeable material except for a semi-permeable membrane as an insert 53 and the outer wall 54 is impermeable when the device is first applied to the skin. As shown in FIG. 15 when compression is applied to the device fractures 56 appear in the outer wall 54 and elastic deformation of the inner wall 52 allows the agent in the reservoir 48 to move into the space between the two walls by capillary action. From there it diffuses through the fractures 56 in the outer wall into the drug matrix 46. This is a concentration driven process which exhibits zero order kinetics. Its rate of movement is therefore much slower than that of the active agent being transdermally absorbed.

Figure 16:
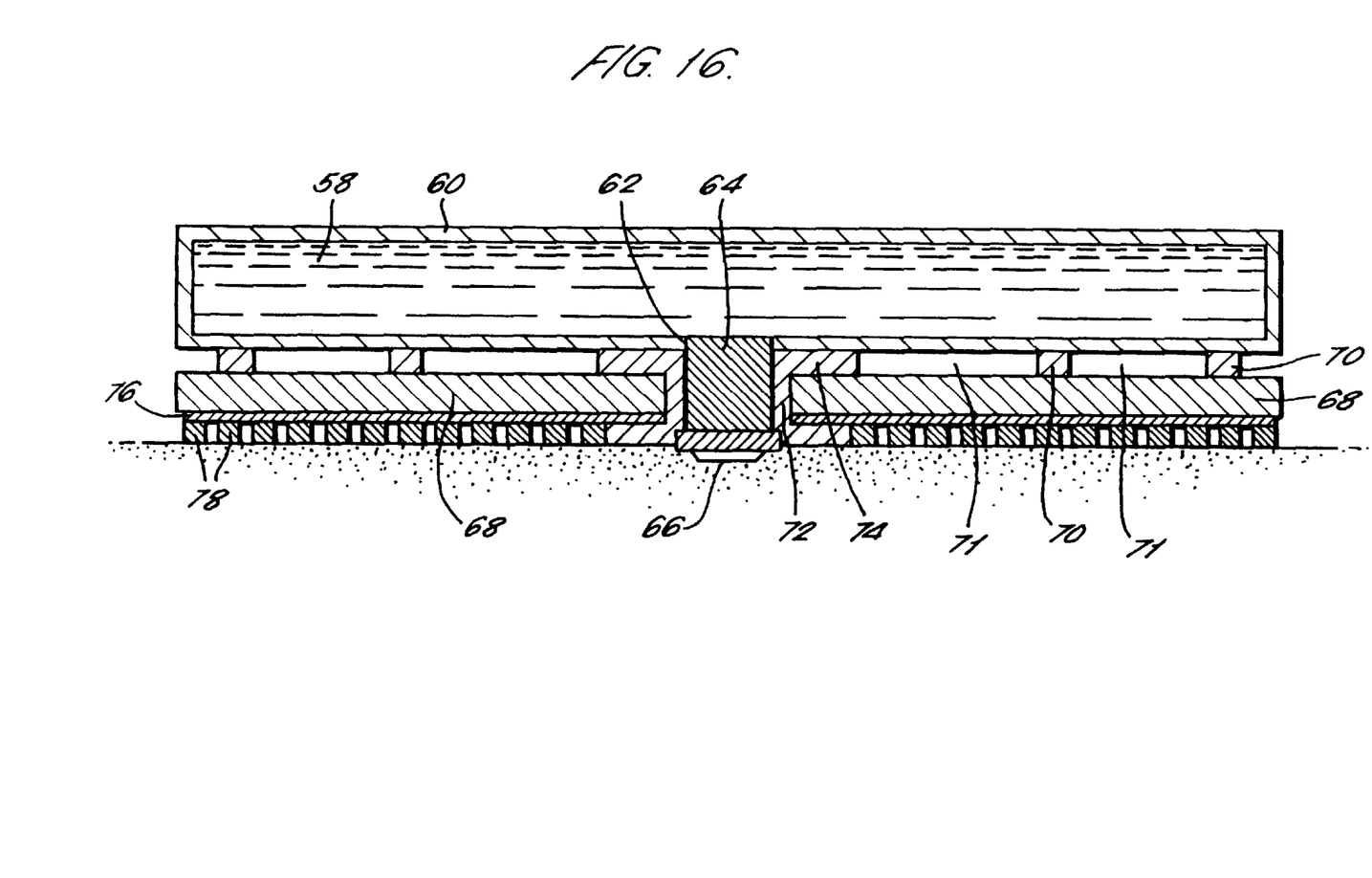

FIG. 16 shows a device in accordance with any aspect of the invention having means for absorbing excess water from the skin without compromising the adhesive. It consists of a drug in a matrix 58 surrounded by an impermeable material 60 except for an outlet 62. Positioned at the outlet is a semi-permeable material such as a hydrogel 64 which will be in contact with the skin lesion 66. The base of the drug reservoir is adhered to the surface of an annular absorbent layer 68 by adhesive blocks 70 so providing air channels 71 therebetween. The central aperture in the layer 68 is lined with a water-resistant adhesive 72 which extends in a flanged formation 74 above and below the absorbent layer. The semi-permeable material 64 protrudes through this adhesive lined aperture to be in contact with the skin lesion 66. The lower surface of the layer 68 is laminated to a porous membrane 76 which in turn supports a porous water resistant adhesive 78 which is applied to the intact skin around the lesion 66.

When the device of FIG. 16 is in use water released from the intact skin is drawn through the porous adhesive 78 and the membrane 76 and soaks into absorbent layer 68. The air spaces 71 prevent ingress of water to the drug reservoir. Such a device may be applied to the skin for many days without skin dampness compromising adhesive strength or the integrity of the device.

EXAMPLE 1

A transdermal device was prepared having the following structure:

5 mls of a hydrogel containing 40 $\mu$g/l 1-deamino-8-D-arginine vasopressin (DDAVP) was laminated between an impermeable layer of aluminized polyester film and a cellulose acetate selective membrane excluding molecular species greater than 70,000 Daltons. This membrane was further laminated to a layer of silicone adhesive having a central aperture devoid of adhesive corresponding to the size of a de-epithelialized skin lesion.

The device was adhered to a de-epithelialized skin lesion of a healthy volunteer and the plasma level of DDAVP measured daily. The results showed an increased absorption on days 1 and 2 which stabilized to a steady state at one third the initial level on days 3 and 4. The device was removed from the skin after four days and no sign of infection was observed. The hydrogel was assessed for breakdown products of DDAVP and these were found to be only 2%. This is in contrast to a breakdown of 10% using a control device of the same construction and under the same conditions but with the cellulose acetate membrane absent.

EXAMPLE 2

A transdermal device was prepared as described in Example 1 except that the cellulose acetate membrane was impregnated with silver chloride and had an average pore size of about 2.0 $\mu$m.

The device was applied to a de-epithelialized skin lesion of a healthy volunteer and plasma concentrations of DDAVP were sampled daily. The results showed increased uptake on days 1 and 2 and then stabilization to a steady state on days 3 and 4 at one third the initial level of uptake. The device was removed after 4 days and no sign of infection was observed. The hydrogel was assessed for bacterial growth and none was found.

EXAMPLE 3

Transdermal uptake of macromolecules through de-epithelialized skin lesions is demonstrated using fluorescein-labelled dextrans having the molecular weight range 3000 to 70,000 Daltons. The experiments were carried out on seven healthy volunteers. The volar side of one forearm was cleansed with cyclohexamide solution. Four suction cups (aperture diameter 6 mm area cm$^2$) were sealed to the skin of each volunteer by adhesive tape and a relative vacuum of 200 mmHg below atmospheric pressure was applied. Within 2 to 3 hours suction blisters were formed painlessly with areas corresponding to the apertures of the suction cup. The epidermal roofs of the blisters were removed and the contained exudate absorbed with a piece of medical gauze. Transdermal devices were applied to the four de-epithelialized lesions on each of the volunteers and one device to intact skin as control. The devices comprised reservoirs fitted with a 6 mm aperture in their base and removable lids.

At t=0 the four reservoirs applied to de-epithelialized lesions were each filled with 0.5 ml of fluoresein-labelled dextran of molecular weights 3000, 10,000, 20,000 and 70,000 respectively. 0.5 ml of fluorescein-labelled dextran of 3000 molecular weight was added to the control reservoir. Uptake of the dextrans into the skin was determined by measuring the decrease in fluorescein in the reservoirs with time using spectrofluorometry at an exitation wavelength of 480 nm and an emission wavelength of 520 nm. Measurements were taken at t=1, 2, 4, 8, 16 and 24 hours. The results are shown in Table 1 below.

TABLE 1

Skin reservoir concentrations ($\mu$M) of the FITC-labelled dextrans with time in human volunteers. Values are given as means ± S.D. (N = 7).

| Test molecule | Time (h) | | | | | |
|---|---|---|---|---|---|---|
| | 1 | 2 | 4 | 8 | 16 | 24 |
| FD-3 | 107.5 | 87.7 | 87.4 | 88.7 | 78.2 | 62.7 |
| | (20.4) | (8.2) | (9.1) | (7.0) | (5.7) | (16.7) |
| FD-10 | 95.3 | 106.5 | 95.9 | 90.1 | 85.2 | 73.8 |
| | (12.9) | (7.0) | (11.2) | (11.4) | (6.7) | (11.9) |
| FD-20 | 123.4 | 119.7 | 119.4 | 109.7 | 88.6 | 77.7 |
| | (13.5) | (10.1) | (5.8) | (8.7) | (30.0) | (28.3) |
| FD-70 | 140.6 | 133.6 | 121.3 | 112.8 | 84.6 | 87.8 |
| | (16.1) | (25.4) | (30.9) | (14.8) | (42.6) | (18.1) |
| FD-3 Control | | | | | | 120.8 |

The results clearly demonstrate substantial transdermal uptake of all the different sized fluorescein-labelled dextrans including dextrans having a molecular weight of 70,000 Daltons, through de-epithelialized skin lesions. The experiment did not demonstrate an upper molecular weight limit for uptake. In contrast uptake from the control reservoir applied to intact skin of a 3000 molecular weight dextran was negligible. Thus suitability of de-epithelialized skin for facilitating transdermal administration of pharmaceuticals which are macromolecules and which are hydrophilic has been demonstrated.

Modifications and variations may be made to the disclosed embodiments without departing from the subject and spirit of the invention as defined by the following claims.

What is claimed is:

1. A transdermal device suitable for administration of a pharmaceutically active agent to the systemic circulation through a de-epithelialized skin lesion, said device including a reservoir for the active agent, said reservoir being selected from the group consisting of an inert porous matrix in which the active agent is dispersed and a chamber containing said agent in a form selected from the group consisting of a solid, an unsaturated solution, a saturated solution, a supersaturated solution and a suspension, said device further including a selective membrane positioned intermediate said reservoir and said de-epithelialized skin so as to be in contact with said de-epithelialized skin when the device is in use, said selective membrane having pores sized so as to block passage of proteolytic enzymes that exude from the de-epithelialized skin while permitting passage of active agent to the skin;
   wherein said selective membrane is cellulose acetate, nitrocellulose, polytetrafluoroethylene, or a swellable hydrogel.

2. A device as claimed in claim 1, wherein said reservoir is an inert porous matrix that is an adhesive.

3. A device as claimed in claim 1, wherein the pharmaceutically active agent is of smaller molecular weight than any proteolytic enzyme in an exudate from the de-epithelialized lesion.

4. A device as claimed in claim 1, wherein said reservoir is an inert porous matrix in which the active agent is dispersed.

5. A device as claimed in claim 1, wherein said device prevents passage of pharmaceutically active agents having a molecular weight of greater than 50,000 Daltons.

6. A device as claimed in claim 1, wherein said device prevents passage of pharmaceutically active agents having a molecular weight greater than 100,000 Daltons.

7. A device as claimed in claim 1, wherein said pore vary in pore size across a depth of said Selective membrane.

8. A device as claimed in claim 1, further including a pre-filter positioned in use between one of said selective membrane and said inert porous matrix and the de-epithelialized skin, said pre-filter having larger pore size than the selective membrane or inert porous matrix.

9. A device as claimed in claim 8, wherein said pre-filter comprises a material selected from a group consisting of cellulose ester, polypropylene and polyvinylidene difluoride.

10. A device as claimed in claim 1, further including means to inhibit activity of proteolytic enzymes.

11. A device as claimed in claim 10, wherein said device includes at least one inhibitor of a proteolytic enzyme.

12. A device as claimed in claim 11, wherein said at least one inhibitor is present in said reservoir.

13. A device as claimed in claim 11, wherein said inhibitor of proteolytic enzyme is dispersed in said selective membrane.

14. A device as claimed in claim 11, wherein said at least one inhibitor inhibits at least one enzyme selected from a group consisting of aminopeptidase, carboxylpeptidase, endopeptidase, metalloprotease, dipeptidylpeptidase, elastase, collaginase, plasmin and plasminogen activator.

15. A device as claimed in claim 14, wherein said at least one enzyme inhibitor is selected from a group consisting of bestatin, phosphoramydon, a2-macroglobulin, sodium ethylenediaminetetracetatic acid, amastatin anti-plasmin, cholate, and analogs of cholate.

16. A device as claimed in claim 1, wherein said pharmaceutically active agent is encapsulated in microspheres of an inert porous polymer material.

17. A device as claimed in claim 1, wherein said pharmaceutically active agent in encapsulated in liposomes.

18. A device as claimed in claim 1, wherein said pharmaceutically active agent is modified so as to be resistant to attack by proteolytic enzymes.

19. A device as claimed in claim 1, wherein said pharmaceutically active agent is selected from a group consisting of vasopressin, human growth hormone, insulin, interferon, erythropoietin and calcitonin.

* * * * *